United States Patent [19]

Khovaylo

[11] 4,241,463
[45] Dec. 30, 1980

[54] PROSTHETIC IMPLANT DEVICE

[75] Inventor: Modest Khovaylo, Old Bridge, N.J.

[73] Assignee: Precision Cast Specialties, Inc., Emerson, N.J.

[21] Appl. No.: 951,883

[22] Filed: Oct. 16, 1978

[51] Int. Cl.³ .............................................. A61F 1/03
[52] U.S. Cl. ............................. 3/1.913; 128/92 CA; 403/135; 403/143
[58] Field of Search .................... 3/1.9, 1.91, 1.911, 3/1.912, 1.913; 128/92 CA; 403/143, 135, 140, 122, 326

[56] References Cited

U.S. PATENT DOCUMENTS

| | | | |
|---|---|---|---|
| 3,683,421 | 8/1972 | Martinie | 3/1.913 |
| 3,787,128 | 1/1974 | Maistrelli | 403/135 |
| 3,813,699 | 6/1974 | Giliberty | 3/1.913 |
| 3,862,807 | 1/1975 | Doden et al. | 403/135 |
| 3,863,273 | 2/1975 | Averill | 3/1.913 X |
| 4,044,403 | 8/1977 | D'Errico | 3/1.913 |
| 4,051,559 | 10/1977 | Pifferi | 3/1.912 |

Primary Examiner—Clifford D. Crowder

[57] ABSTRACT

A prosthetic joint for use in replacing the ball end of a biological joint, the replacement including a spherical head for insertion into a natural socket, an insert in the head and locked therein by an inwardly projecting ring in the head and a groove in the insert, a ball shaped member seated in the insert and having a neck and a stem for mounting the joint on the end of the biological member on which the ball is being replaced and a ring having a downwardly and inwardly sloping outer wall seating in a recess in the plastic insert and locking the ball shaped member in the insert.

15 Claims, 5 Drawing Figures

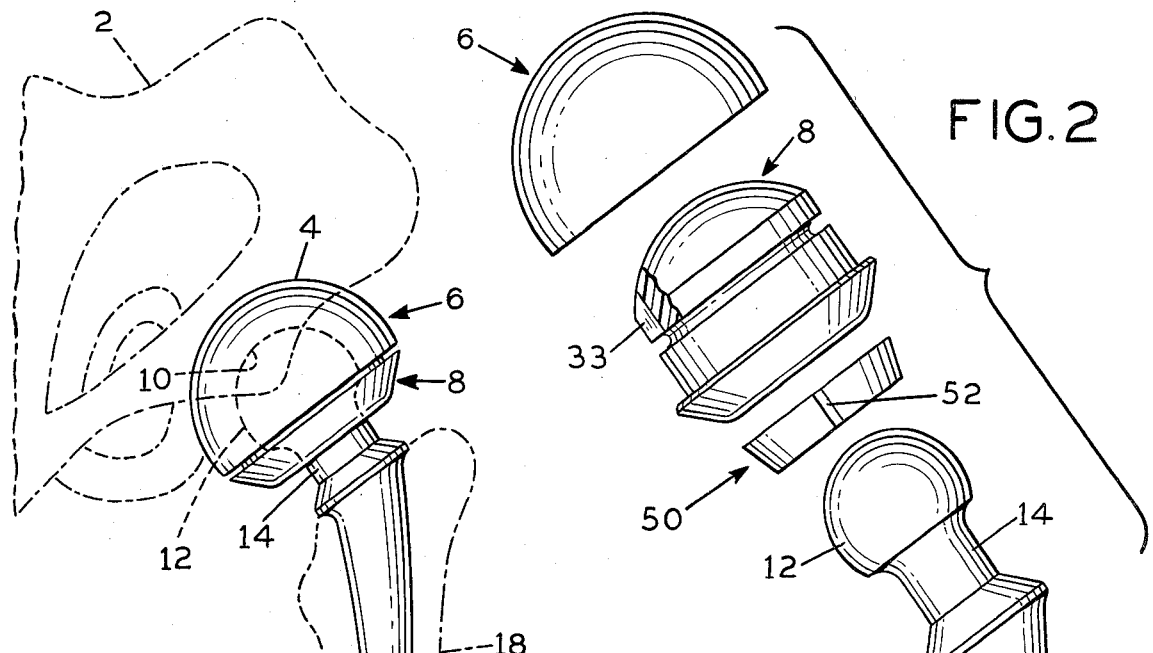
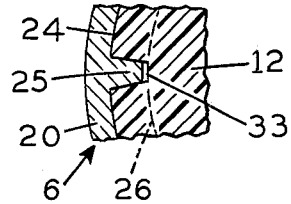
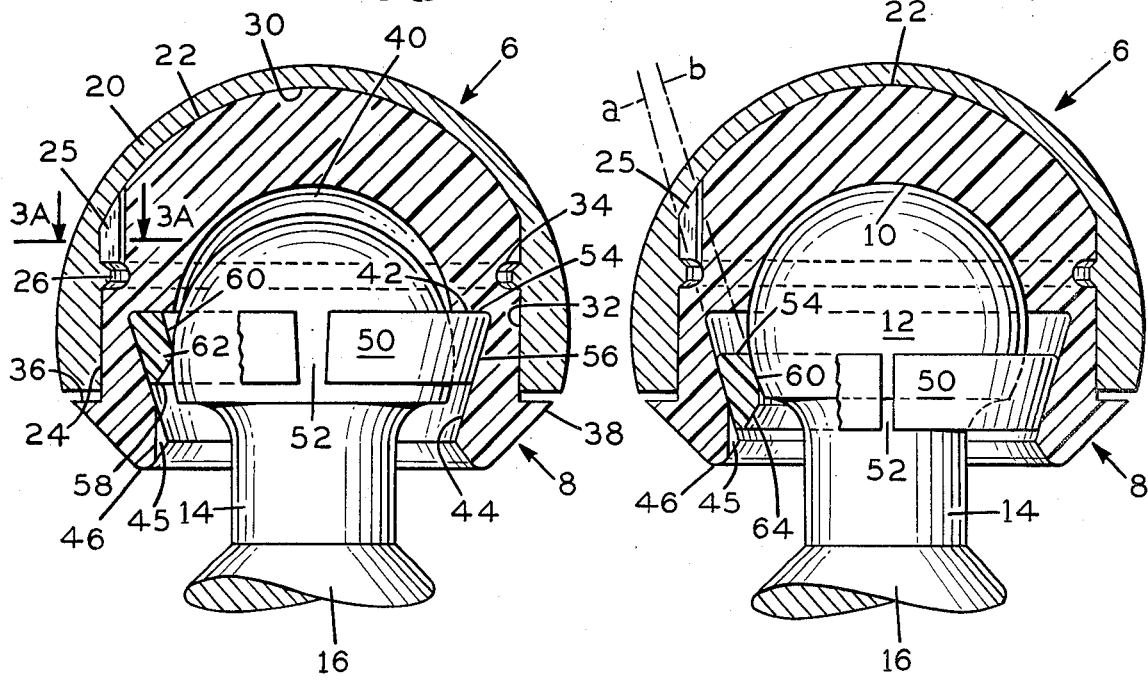

PROSTHETIC IMPLANT DEVICE

This invention relates to femoral hip prosthesis, and, more particularly, to a femoral head and neck prosthesis for implant and interaction with the natural bone structure of the pelvic acetabulum.

The pelvis in the human body contains two hip bones, one on each side of the body and each containing an acetabulum or hip socket for receiving and forming a seat for the femoral head, or ball, of the femur or thigh bone. The femoral head is connected to the thigh bone by a neck which is angularly disposed relative to the axis of the femur and relative to the vertical axis of the body. Thus, any load applied by the body through the hip and femur neck to the thigh bone and leg and any impacts, such as in walking, jumping and the like, applied by the leg and thigh bone through the femur neck and hip to the body are transmitted angularly through the femur neck. This angular transmitting of the load and forces through the femur neck results in high stresses and high sheer loads applied to the femur neck. These high stresses, abnormally applied, can cause dislocation of the femoral head from the acetabulum or hip socket and fracture and breaking of the femur neck. In older people, such femur neck often becomes brittle and, in both older and younger people is subject to injury. Replacement is often required.

In some instances, both the acetabulum or hip socket and the femoral head or ball and neck require replacement. In other instances, where injury or damage is limited to the femoral head and femur neck, only the head and neck require replacement. The replacement of the femoral head and neck without the replacement of the acetabulum is, of course, a much easier surgical procedure and desirable.

Various attempts have, heretofore, been made to provide femoral head and necks for surgical implant in the natural acetabulum and replacement of the natural head and neck damaged or broken. Thus, in U.S. Pat. Nos. 3,813,699 and 3,863,273 there are shown and described femoral heads and necks for such surgical implant and replacement for damaged or broken natural heads or necks. In both such devices, an outer spherical metal cup, having an inner plastic insert, is provided for implanting in the acetabulum or hip socket. The inner plastic insert has a socket into which a metal sphere, having a neck and a stem for connection to the thigh bone, is pivotally received.

While the devices of such patents provide replacements for surgical implant when the natural femoral head or neck are broken or damaged, such devices can become displaced after implant. Thus, the outer spherical metal cup may become displaced from the hip socket, the inner plastic insert may become displaced from the outer cup or the metal sphere may become displaced from the plastic insert. Such displacement may arise when the leg or body is abnormally twisted much in the same manner as might result in dislocation in the normal hip in a person having a propensity for hip dislocation. The difficulty in such patented devices when dislocation occurs is in the relocation of the implant once dislocation occurs without resort to new surgery. While the parts dislocated might be identified in the customary manner, such as by x-ray, such devices do not readily lend themselves to relocation without surgery. This is because, in attempting to realign or relocate the dislocated elements with each other, such as by twisting or pulling in the conventional manner, other parts in the device, at the time aligned and properly located, can be misaligned and dislocated, compounding rather than correcting the original dislocation. Such compounding can require surgical correction. Furthermore, in attempting to relocate and realign the devices of the patents, damage to the natural bone and body tissues in the vicinity of the joint may also result.

In the instant invention, many of the difficulties heretofore encountered in providing an implantable replacement for the femoral head and neck for use with the natural acetabulum or hip joint are overcome. While still employing an outer spherical cup, an inner insert and a metal sphere having a neck and a stem for connection to the thigh bone, the cup, insert and sphere are interconnected and implanted in the natural acetabulum in such a manner that dislocation or misalignment of the component parts, one to the other, is avoided. Furthermore, the various components are shaped and assembled so as to avoid contact between the hard edges with bone and body tissue should dislocation of the assembly and the natural acetabulum or hip socket arise and relocation and realignment, such as through twisting and pulling, become necessary.

The femoral head and neck prosthetic implant of the instant invention includes an outer spherical cup, an inner insert and a metal sphere having a neck and a stem for connection to the thigh bone and for insertion into a socket in the inner insert. The outer cup may be of metal and the inner insert may be of plastic and the cup and insert may be interconnected by a mating protruberance and groove and the plastic insert extends outwardly and along the edge of the metal cup for purposes more fully described later herein. The outer cup and the inner insert may be of one piece such as of impact and abrasive resistant ceramic having a low coefficient of friction. The lower or entry end of the inner insert socket is tapered and slopes downwardly and inwardly toward the socket open end. A plastic split ring, having a sloping outer wall corresponding with the slope on the wall of the insert and a curved inner wall for seating on the spherical surface of the metal sphere are provided between the metal sphere and the insert so that the metal sphere might be inserted into the insert and, once in place, will be locked for pivotal movement in the insert.

The invention of the instant application will be more fully discussed and better understood from the following description, taken with the appended drawings, in which FIG. 1 is a view, in full and phantom lines and taken from the front, showing in phantom line, the natural pelvis, acetabulum, and thigh bone and, in full line, the implant device of the instant invention;

FIG. 2 is an enlarged exploded view, of the implant device of the instant invention showing the parts in their relative assembly position;

FIG. 3 is an enlarged view, partly in section, showing the outer spherical cup, the inner plastic insert, the metal sphere and neck, as the metal sphere is being inserted into the outer spherical cup and plastic insert assembly;

FIG. 3A is a sectional view taken at 3A—3A FIG. 3; and

FIG. 4 is an enlarged view, similar to FIG. 3 but showing the metal sphere, outer cup and plastic insert assembled.

Referring to the drawings, the pelvis, generally designated 2, has an acetabulum or hip socket 4. The spherical cup, generally designated 6, has an insert, generally designated 8, seated in sphere 6 and in turn having a socket 10 for receiving sphere 12, having a neck 14 and stem 16 for implant in thigh bone 18.

The materials of spherical cup 6, insert 8, sphere 12, neck 14 and stem 16 may be of any material compatible with bone and body tissues of the patient in which the implant device of the instant invention is to be implanted and of sufficient strength to withstand forces which will be encountered. Cup 6 and insert 8 may be of one piece and of impact, wear and abrasive resistant ceramic and neck 14 and stem 16 might be of metal. Preferably, spherical cup 6, sphere 12, neck 14 and stem 16 are of a metal material. Materials such as cobalt chrome molybdenum alloy ASTM F-75 and stainless steel ASTM F-139-71 are especially suited for this purpose. Insert 8 is preferably made from a low-friction material having sufficient strength, abrasive resistance and rigidity to accomodate the forces which will be applied. Ultra-high molecular weight polyethylene is a material suitable for this purpose.

Referring, now, to FIGS. 3 and 4, spherical cup 6 has an outer spherical surface 20 and an inner spherical dome 22. Spherical dome 22 terminates in a cylindrical skirt 24, extending downwardly from the dome to the open end of the spherical cup 6. Just below the point where dome 22 joins cylindrical skirt 24, skirt 24 is provided with a key 25 and an inwardly extending protuberance or ring 26 extending circumferentially around skirt 24. The outer surface of plastic insert 8 is shaped to the configuration of the inner surface of spherical cup 6. Thus, insert 8 has an outer spherical dome 30, and downwardly and cylindrically extending skirt 32, keyway 33 and recess 34 into which the key and protuberance on spherical cup 6 extend when plastic insert 8 is inserted in spherical cup 6 as shown in FIGS. 3 and 4. At its lower end, below skirt 32, the outer wall of plastic insert 8 extends outwardly at 36, along the bottom wall of spherical cup 6 and then slopes downwardly and inwardly, at 38 to the open end of insert 8.

The inner surface of plastic insert 8 is domed at 40 to receive spherical head 12. Below dome 40, the inner wall on insert 8 extends outwardly at 42 and then slopes downwardly and inwardly at 44 where it joins the outer wall rounded at 46. At its lower end, wall 44 is provided with a slot 45. For reasons which will be more apparent later herein, the slope of wall 44 and slot 45 are of substantial importance.

A ring, generally designated 50, preferably of the same plastic material as the plastic material of the insert and having a split at 52, has a top wall 54, a downwardly and inwardly sloping outer wall 56 of the same slope as wall 44 of insert 8 and for mating engagement therewith, a bottom wall 58 and an inner wall curved at 60 to mate with the wall of spherical head 12 when insert 50 is in the downward locked position, in FIG. 4, an intermediate portion 62 to mate with the spherical surface of sphere 12 as the sphere is being inserted into insert 8, through ring 50, FIG. 3 and a tapered bottom wall 64 joining curved inner wall portion 62 with bottom wall 58.

The slope of inner wall 44 of insert 8 and the slope of outer ring wall 56 and of ring 50, taken with the slope of the line drawn through the upper and lower points of contact between curved inner wall 60 of ring 50 and the surface of sphere 12 is such that when the lines formed thereby are extended upwardly and through insert 8 and spherical cup 6, such lines converge. Thus, as shown at lines a, b, FIG. 4 formed by the upward projection of the slope of insert wall 44, ring wall 56 and the upward projection of a line drawn through the upper and lower extremities of the line of contact between inner wall 60 of ring 50 and the surface of sphere 12, with ring 50 and sphere 12 in place, as shown in FIG. 4, sphere 12 tends to force or urge ring 12 downward along wall 44 of insert 8, wedging ring 50 between wall 44 and sphere 12 and locking sphere 12 in the domed cavity of insert 8 when disassembly is attempted. The greater the force applied by sphere 12 to split ring 50, such as the force applied which could otherwise dislocate sphere 12, the greater the wedging force applied to ring 50 by sphere 12 and the greater the resistance to the displacement or dislocation of sphere 8 from insert 8 and cup 6.

The femoral hip prosthesis device of the instant invention is assembled by first inserting plastic insert 8 into spherical cup 6 and then snapping ring 26 on cup 6 into recess 34 in insert 8. Insert 8 is then locked in cup 6 with spherical dome 30 of insert 8 in contact with inner spherical dome 22 of cup 6. Sloping wall 38 of insert 8 slopes downwardly and inwardly below the end wall of metal, spherical cup 6, preventing contact of such cup end wall with bone and body tissue, as will be later described.

With insert 8 in cup 6 and locked therein by the interengagement of cup ring 26 with insert recess 34, split ring 50 is inserted through the open end of plastic insert 8 and the end of sphere 12 is inserted into the open end of insert 8. As the dome of sphere 12 enters the cavity in insert 8 and contacts wall 69 of ring 50, ring 50 is raised, wall 54 of ring 50 engages inwardly extending wall 42 of insert 8 and ring 50 expands, allowing sphere 12 to enter the cavity of insert 8 and permitting the spherical surface of sphere 12 to be brought into contact with spherical dome 40 in insert 8. With the dome of sphere 12 in contact with spherical dome 40 of insert 8, the memory of the split ring causes split ring 50 to contract and slide downwardly along sloping wall 44 and locking sphere 12 in insert 8. As has already been noted, the wedging of ring 50 between insert wall 44 and sphere 12 locks sphere 12 in the domed cavity of insert 8 and prevents sphere 12 from being displaced or dislocated from insert 8 and cup 6.

In surgical implant of the device, cup 6 and insert 8 might be assembled and positioned in the acetabulum or hip socket 4. Sphere 12, neck 14 and stem 16 might then be fixed to the thigh bone by implanting stem 16 in thigh bone 18. Next, split ring 50 and sphere 12 might be assembled in the cup 6 already assembled in insert 8 in hip socket 4. The prosthetic device of the invention might also be fully assembled, stem 16 inserted and attached to thigh bone 18 and the outer spherical surface 20 of cup 6 might then be inserted into the acetabulum or hip socket 4.

Once assembled, spherical cup 6, plastic insert 8 and sphere 12, with neck 14 and stem 16, function as a unit. That is, sphere 12 cannot be removed or displaced from insert 8 and insert 8, with sphere 12 in place, cannot be separated or dislocated from cup 6. Thus, any unusual force which might be applied to the prosthetic device of the instant invention, once the device is surgically implanted which would cause displacement or dislocation, will result in the dislocation of the prosthetic hip joint of the invention as a unit much in the same manner as would occur at the joint in a natural hip. In other words, the device of the instant invention will remain as a unit and will be displaced as a unit from the acetabulum or hip socket 4 at cup 6. The hip prosthesis of the instant invention, should it become displaced or dislocated, can be restored to its proper position by manipulating the leg or thigh bone in the same manner as in the relocation of a dislocated natural hip. The sloping wall 38 of the plastic insert, extending over and covering the end of the spherical cup 6, guides the prosthetic device back into place and prevents damage to body and bone tissue when the prosthetic device of the instant invention is being manipulated, in conventional manner, to relocate a displaced hip joint.

Once the device of the instant invention has been assembled and surgically implanted, disassembly of the device should not be necessary. However, should it become necessary or desirable to disassemble the unit, a screw driver or surgical instrument can be inserted through slot 45 at the end of sloping wall 44 of insert 8 and split ring 50 can be forced upwardly and expanded outwardly around sphere 12. A plurality of such slots spaced around split ring 50 may be provided to better guide and expand the split ring during such expansion. With split ring 50 elevated in insert 8, as shown in FIG. 3, sphere 12 can be withdrawn, through split ring 50, from insert 8.

The terms and expressions which have been employed are used as terms of description and not of limitation, and there is no intention, in the use of such terms and expressions, of excluding any equivalents of the features shown and described or portions thereof, but it is recognized that various modifications are possible within the scope of the invention claimed.

What is claimed:

1. An implantable prosthetic joint for use in replacement of the ball end of a biological joint, said prosthetic joint having a metal spherical head for insertion into and seating in the natural socket of the joint, a bearing insert in said spherical head, said bearing insert having an outer spherical dome for engagement with the inner surface of said metal spherical head, an inner spherical dome and an outwardly extending recess at the entrance end of said inner spherical dome extending circumferentially around said entrance end and having an outwardly extending end wall and an outer wall extending downwardly from said end wall and sloping downwardly and inwardly toward said entrance, a ball shaped member seated in said inner spherical dome of said bearing insert and a ring intermediate said bearing insert and said ball shaped member, said ring having an end wall and an outer wall sloping downwardly and inwardly and in contact with said outer wall of said insert recess and an arcuate wall in contact with said ball shaped member, the length of said outer sloping wall of said ring being substantially shorter than the outer sloping wall of said recess in said bearing insert and permitting said ring to slide upwardly and expand in said recess in said bearing insert until said ball passes through said ring as said ball shaped member is inserted through the entrance end into said insert and to permit said ring to slide downwardly in said recess away from said recess end wall and wedge between said outer sloping wall of said recess and said ball shaped member when force is applied to said ball shaped member to withdraw said ball shaped member from said insert to lock said ball shaped member in said bearing insert and to permit said ring to be pushed by an unlocking tool upwardly in said recess in said bearing insert toward said outwardly extending end wall of said recess to permit said ring to be expanded outwardly sufficiently for said ball shaped member to be withdrawn through said ring and from said insert.

2. An implantable prosthetic joint, as recited in claim 1, in which said ring is a split ring.

3. An implantable prosthetic joint, as recited in claim 2, in which said outer sloping wall of said recess at the entrance end of said inner spherical dome has a recess for receiving an instrument for sliding said ring upwardly in said recess to release said ball shaped member from contact with said inner spherical dome of said bearing insert.

4. An implantable prosthetic joint, as recited in claim 3, in which the inner surface of said metal spherical head has a downwardly extending skirt and an inwardly extending ring extending circumferentially around said skirt and said bearing insert has an inwardly extending recess for engagement with said inwardly extending ring for locking said bearing insert in said spherical head when said outer spherical dome of said bearing insert is in engagement with the inner surface of said metal spherical head.

5. An implantable prosthetic joint, as recited in claim 4 in which the lines formed by projecting the slope of the outer walls of said insert and said ring and the slope of a line drawn through the end points of the contact of said arcuate wall of said ring with said ball shaped member and extending upwardly through said bearing insert and said metal spherical head merge toward each other.

6. An implantable prosthetic joint as recited in claim 5 in which said bearing insert is of inert, low friction, plastic material.

7. An implantable prosthetic joint, as recited in claim 6 in which said plastic is selected from the group consisting of high molecular weight polyethylene and high molecular weight polypropylene.

8. An implantable prosthetic joint, as recited in claim 1, in which said ball shaped member includes a neck and a stem for mounting said ball shaped member on the biological member on whose end the ball is being replaced.

9. An implantable prosthetic joint, as recited in claim 8, in which said bearing insert has an outwardly extending portion at its entrance end, said outwardly extending portion extending outwardly along the end of said metal spherical head and forming a guard therefor.

10. An implantable prosthetic joint for use in replacement of the ball end of a biological joint, said prosthetic joint having a spherical head for insertion into and seating in the natural socket of the prosthetic joint, a bearing insert in said spherical head having an inner spherical dome and an outwardly extending recess at the entrance end of said inner spherical dome extending circumferentially around said entrance end and having an outwardly extending end wall and an outer wall extending downwardly from said end wall and sloping downwardly and inwardly toward said entrance, a ball shaped member seated in said inner spherical dome of said bearing insert and a ring intermediate said bearing and said ball shaped member, said ring having an end wall and an outer wall sloping downwardly and inwardly and in contact with said outer wall of said insert recess and an arcuate wall in contact with said ball shaped member, the length of said outer sloping wall of said ring being substantially shorter than the outer sloping wall of said recess in said bearing insert and permitting said ring to slide upwardly and expand in said recess in said bearing insert until said ball passes through said ring as said ball shaped member is inserted through the entrance end into said insert and to permit said ring to slide downwardly in said recess away from said recess end wall and wedge betweenn said outer sloping wall of said recess and said ball shaped member when force is applied to said ball shaped member to withdraw said ball shaped member from said insert to lock said ball shaped member in said bearing insert and to permit said ring to be pushed by an unlocking tool upwardly in said recess in said bearing insert toward said outwardly extending end wall of said recess to permit said ring to be expanded outwardly sufficiently for said ball shaped member to be withdrawn through said ring and from said insert.

11. An implantable prosthetic joint, as recited in claim 10, in which said ring is a split ring.

12. An implantable prosthetic joint, as recited in claim 11, in which said outer sloping wall of said recess at the entrance end of said inner spherical dome has at least one recess for receiving an instrument for sliding said ring upwardly in said recess to release said ball shaped member from contact with said inner spherical dome of said bearing insert.

13. An implantable prosthetic joint, as recited in claim 12 in which the lines formed by projecting the slope of the outer walls of said insert and said ring and the slope of a line drawn through the end points of contact between the arcuate wall of said ring with said ball shaped member upwardly through said spherical head converge toward each other.

14. An implantable prosthetic joint, as recited in claim 10, in which said ball shaped member includes a neck and a stem for mounting said ball shaped member on the biological member on whose end the ball is being replaced.

15. An implantable prosthetic joint, as recited in claim 14, in which said insert has an outwardly extending portion at its entrance end, said outwardly extending portion extending outwardly along the end of said spherical head and forming a skid therefor.

* * * * *